United States Patent
Kim et al.

(10) Patent No.: US 7,964,605 B2
(45) Date of Patent: Jun. 21, 2011

(54) PHENYL PIPERAZINE COMPOUNDS, PHARMACEUTICAL COMPOSITION COMPRISING THE SAME, AND USE THEREOF

(75) Inventors: Yonggil Kim, Daejeon (KR); Kiho Lee, Daejeon (KR); Nahmryune Cho, Daejeon (KR); Jin Uk Yoo, Daejeon (KR); Joon Heo, Daejeon (KR); Choonho Ryu, Daejeon (KR); Seonmin Dong, Gyeonggi-do (KR); Man-Young Cha, Daejeon (KR); Jong Gil Choi, Daejeon (KR); Yunhee Kim, Gyeonggi-do (KR); Mi Kyung Ji, Daejeon (KR)

(73) Assignee: SK Holdings Co., Ltd., Seoul (KR)

( * ) Notice: Subject to any disclaimer, the term of this patent is extended or adjusted under 35 U.S.C. 154(b) by 207 days.

(21) Appl. No.: 12/128,999

(22) Filed: May 29, 2008

(65) Prior Publication Data

US 2009/0298851 A1 Dec. 3, 2009

(51) Int. Cl.
*A61K 31/4965* (2006.01)
*C07D 241/04* (2006.01)
*C07D 295/00* (2006.01)

(52) U.S. Cl. .................. 514/255.03; 544/393

(58) Field of Classification Search ............. 514/255.03; 544/393
See application file for complete search history.

(56) References Cited

U.S. PATENT DOCUMENTS

| | | | |
|---|---|---|---|
| 4,975,445 A | 12/1990 | Caprathe et al. | |
| 5,006,528 A | 4/1991 | Oshiro et al. | |
| 2004/0001492 A1 | 1/2004 | Johnson | |
| 2009/0253710 A1* | 10/2009 | Liotta et al. ............. | 514/253.01 |

FOREIGN PATENT DOCUMENTS

| | | |
|---|---|---|
| WO | 98/18797 A | 5/1998 |
| WO | 98/42692 A | 10/1998 |
| WO | 2004/112729 A | 12/2004 |
| WO | 2009/145591 A | 5/2009 |

OTHER PUBLICATIONS

Agarwal, et al., Synthesis and structure activity relationship in 1-(substituted aminophenoxy)-3-[N1-(N4-arylpiperazinyl)]propanes, Indian Journal of Chemistry, Section B: Organic Chemistry Including Medicinal Chemistry, 21B(10), 914-18 (1982).*
Sukalovic, et al., "Synthesis, dopamine D2 receptor binding studies and docking analysis of 5-[3-(4-arylpiperazin-1-yl)propyl]-1H-benzimidazole, 5-[2-(4-arylpiperazin-1-yl)ethoxy]-1H-benzimidazole and their analogs" European Journal of Medicinal Chemistry 2005, 40: 481-493.
Kowalski, et al., "The Synthesis of Cyclic and Acyclic Long-chain Arylpiperazine Derivatives of Salicylamides as Serotonin Receptor Ligands" Journal of Heterocyclic Chemistry, Jan.-Feb. 2008, 39(1), 209-214.
International Search Report for Application No. PCT/KR2009/002881 dated Jan. 7, 2010 (2 pages).

* cited by examiner

*Primary Examiner* — James O Wilson
*Assistant Examiner* — Erich A Leeser
(74) *Attorney, Agent, or Firm* — Michael Best & Friedrich LLP

(57) ABSTRACT

The present invention relates to a novel piperazine derivative or pharmaceutically acceptable salt thereof, a process for preparing the same, a pharmaceutical composition for treating central nervous system diseases comprising an effective amount of the piperazine compound and a method of treating central nervous system (CNS) disorder such as psychosis in a mammal.

10 Claims, No Drawings

PHENYL PIPERAZINE COMPOUNDS, PHARMACEUTICAL COMPOSITION COMPRISING THE SAME, AND USE THEREOF

FIELD OF THE INVENTION

The present invention relates to a novel piperazine derivative or pharmaceutically acceptable salt thereof, a process for preparing the same, a pharmaceutical composition for treating central nervous system diseases including an effective amount of the piperazine compound, and a method of treating central nervous system (CNS) disorders such as psychosis in a mammal.

BACKGROUND OF THE INVENTION

Many reports have disclosed that phenyl piperazine compounds are effectively used for controlling various central nervous system (CNS) disorders, especially psychoses, schizophrenia, depression, and anxiety.

7-[4-[4-(2,3-dichlorophenyl)-piperazin-1-yl]butoxy]-1,2,3,4-tetrahydroquionlin-2-onedines were disclosed in U.S. Pat. No. 5,006,528, (2-pyridinyl)-4-[4-(2-pyridinyl)-3-cyclohexen-1-yl]-piperazines were disclosed in U.S. Pat. No. 4,975,445, and 4-[4-(quinolin-8-yl)-piperazin-1-yl]-1-(4-fluorophenyl)butan-1-ones or ols were disclosed in U.S. Publication No. 2004/0014972A1.

These compounds are found to be very effective as therapeutical medicines for managing CNS diseases, such as psychosis, schizophrenia, depression, and anxiety. Active research and development efforts have continued to be directed to the application of phenyl piperazine compounds for the treatment of CNS disorders.

SUMMARY OF THE INVENTION

A principal object of the present invention is to provide a novel piperazine derivative and a pharmaceutically acceptable salt thereof, and a process of the piperazine derivative.

It is another object of the present invention to provide a pharmaceutical composition including an effective amount of phenyl piperazine or a pharmaceutically acceptable salt thereof for treating CNS disorders such as psychosis and cognition disorders such as psychosis, schizophrenia, depression, and anxiety.

It is still another object of the present invention to provide a method of treating CNS disorders such as psychosis, schizophrenia, depression, and anxiety in a mammal including administering an effective amount of a piperazine compound or a pharmaceutically acceptable salt thereof, alone or in combination with a pharmaceutically acceptable carrier or excipient to a mammal in need.

DETAILED DESCRIPTION OF THE INVENTION

Novel compounds of the invention have the Structural Formula (I) and pharmaceutically acceptable salts thereof.

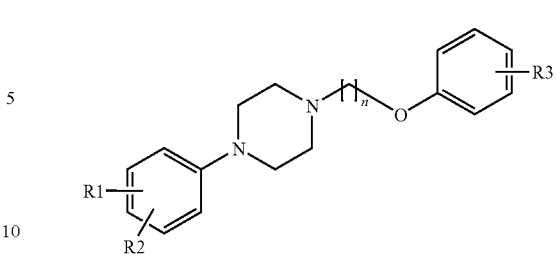

Herein,
n is an integer from 2 to 6,
$R_1$ and $R_2$ are the same or different and are independently selected from the group consisting of hydrogen, a hydroxyl, a halogen, nitrogen dioxide, a straight or branched chain alkyl group with 1 to 4 carbon atoms, and a straight or branched chain alkoxy group with 1 to 4 carbon atoms, and
$R_3$ is selected from the following groups:

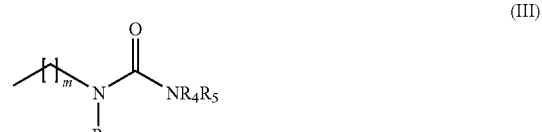

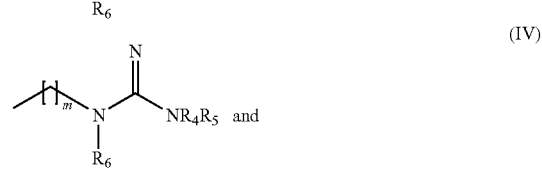

wherein
m is an integer from 1 to 3,
$R_4$ and $R_5$ are the same or different and are independently selected from the group consisting of hydrogen, a straight or branched chain alkyl group with 1 to 4 carbon atoms and benzyl, and optionally $R_4$ and $R_5$ form a 5 to 7-membered heterocyclic ring together with nitrogen atoms to which they are attached,
$R_6$ is selected from the group consisting of hydrogen, a straight or branched chain alkyl group of from 1 to 4 carbon atoms and phenyl.

More specifically, the exemplary piperazine compounds represented by the Formula (I) include the compounds represented by the following Structural Formulae (VII), (IX), and (X):

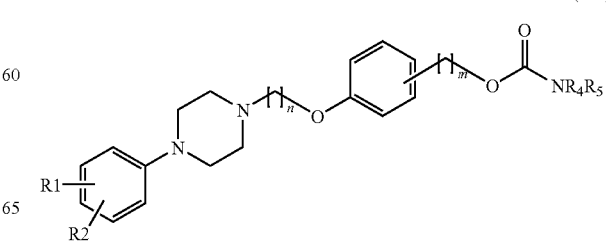

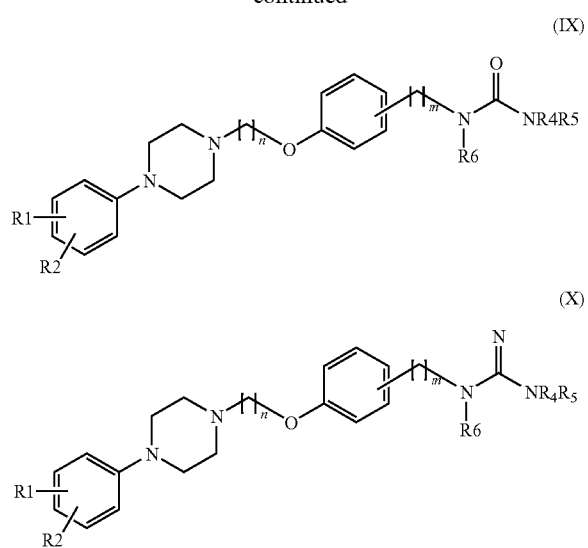

In the compounds having Formulae (VII), (IX), and (X), the definitions of R1, R2, R4, R5, R6, n, and m are defined above.

Examples of said alkyl include methyl, ethyl, n-propyl, isopropyl, n-butyl, iso-butyl, sec-butyl, and t-butyl. Preferred alkyl groups are methyl, ethyl, propyl, isopropyl, and tertiary butyl. Unless otherwise stated or indicated, the term "alkoxy" denotes a group O-alkyl, wherein alkyl is as defined above. Unless otherwise stated or indicated, the term "halogen" shall mean fluorine, chlorine, bromine, or iodine.

The most preferred compounds having Chemical Formula (VII) are carbamic acid 4-{4-[4-(2-methoxy-phenyl)-piperazin-1-yl]-butoxy}-benzyl ester, carbamic acid 4-{3-[4-(2-methoxy-phenyl)-piperazin-1-yl]-propoxy}-benzyl ester, carbamic acid 4-{2-[4-(2-methoxy-phenyl)-piperazin-1-yl]-ethoxy}-benzyl ester, carbamic acid 4-{5-[4-(2-methoxy-phenyl)-piperazin-1-yl]-pentyloxy}-benzyl ester, and carbamic acid 4-{4-[4-(2-fluoro-phenyl)-piperazin-1-yl]-butoxy}-benzyl ester.

The most preferred compounds having Chemical Formula (IX) are (4-{4-[4-(2-methoxy-phenyl)-piperazin-1-yl]-butoxy}-benzyl)-urea, (3-{4-[4-(2-methoxy-phenyl)-piperazin-1-yl]-butoxy}-benzyl)-urea, and 1-(4-{4-[4-(2-chloro-phenyl)-piperazin-1-yl]-butoxy}-benzyl)-1-methyl-urea.

The most preferred compounds having Chemical Formula (X) are N-(4-{4-[4-(2-methoxy-phenyl)-piperazin-1-yl]-butoxy}-benzyl)-guanidine, and N-(3-{4-[4-(2-methoxy-phenyl)-piperazin-1-yl]-butoxy}-benzyl)-guanidine.

Representative examples of the compounds of Formulae (I), (VII), (IX), and (X) prepared according to reaction scheme I, II, III, IV, V, and VI include the following structures:

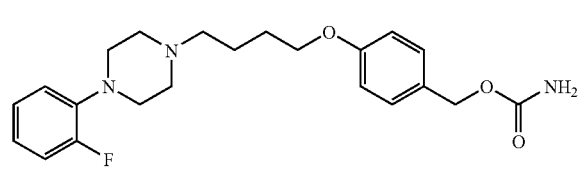

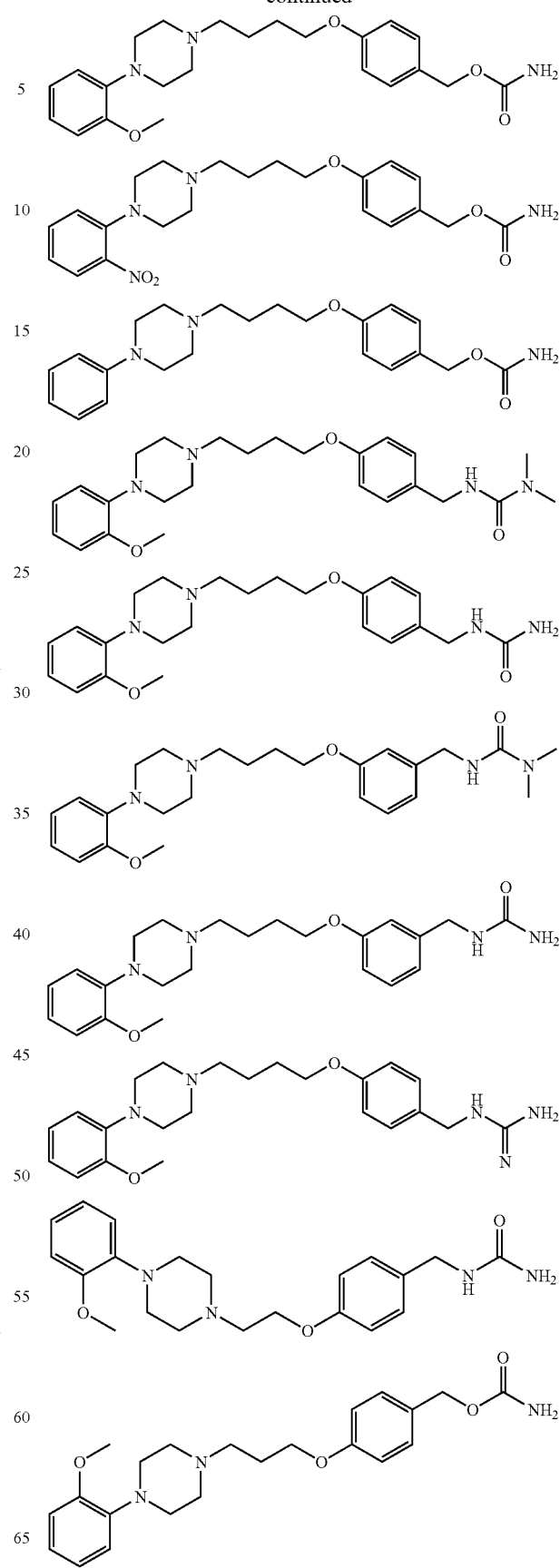

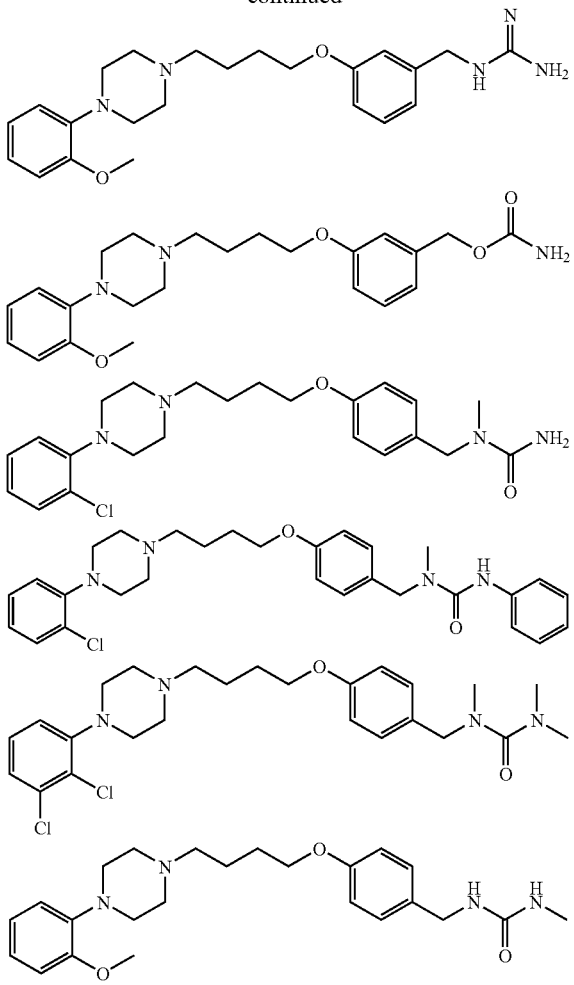

A "pharmaceutically acceptable salt", where such salts are possible, includes both pharmaceutically acceptable acid and base addition salts. A suitable pharmaceutically acceptable salt of a compound of Formula I is, for example, an acid-addition salt of a compound of Formula I that is sufficiently basic, for example an acid-addition salt with an inorganic or organic acid such as hydrochloric, hydrobromic, sulphuric, trifluoroacetic, citric or maleic acid; or, for example, a salt of a compound of Formula I that is sufficiently acidic, for example an alkali or alkaline earth metal salt such as a sodium, calcium, or magnesium salt, or an ammonium salt, or a salt with an organic base such as methylamine, dimethylamine, trimethylamine, piperidine, morpholine, or tris-(2-hydroxyethyl)amine.

Throughout the specification and the appended claims, a given chemical formula or name shall encompass all stereo and optical isomers and racemates thereof as well as mixtures in different proportions of the separate enantiomers, where such isomers and enantiomers exist, as well as pharmaceutically acceptable salts thereof and solvates thereof such as, for instance, hydrates. Isomers may be separated using conventional techniques, e.g. chromatography or fractional crystallization. The enantiomers may be isolated by separation of racemates for example by fractional crystallization, resolution, or HPLC. The diastereomers may be isolated by separation of isomer mixtures for instance by fractional crystallization, HPLC, or flash chromatography.

The piperazine compounds represented by Formula (I) can be produced using hydroxy compounds represented by the General Structural Formula (XI) as intermediates.

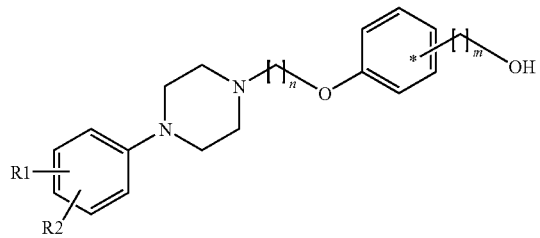

Wherein R1 and R2 are the same as defined above.

To produce the hydroxyl compounds represented by the general formula (XII), a reacting phenols represented by Formula (XII) a below are used as starting material. In some cases, the reacting phenols represented by Formula (XII) can be prepared by reacting benzaldehydes represented by Formula (A) with sodium borohydrides:

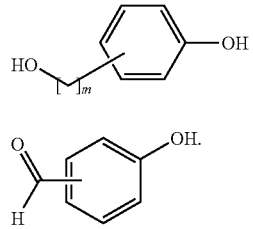

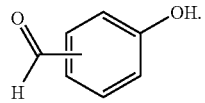

The reacting phenols of Formula (XII) are reacted with dihalide alkanes represented by Formula (XIII) to synthesize halogenized compounds represented by Formula (XIV):

$$X\text{—}(CH_2)n\text{—}X \quad \text{(XIII)}$$

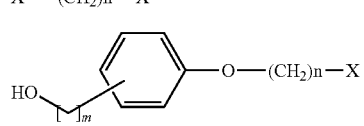

wherein n, m, and X are the same as defined above.

The halogenized compound represented of Formula (XIV) is reacted with phenyl piperazines of Formula (XV) to obtain the hydroxy compounds having hydroxy group represented by the structural Formula (XI):

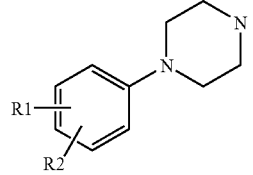

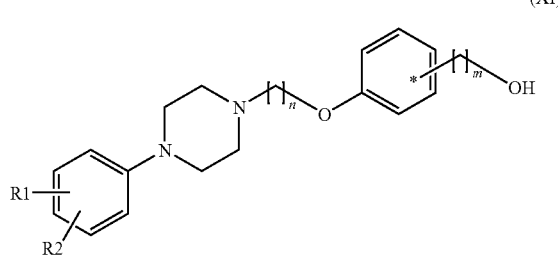

(XI)

wherein R1 and R2 are the same as defined above.

This procedure is summarized as set forth in Reaction Scheme I below.

Reaction Scheme I

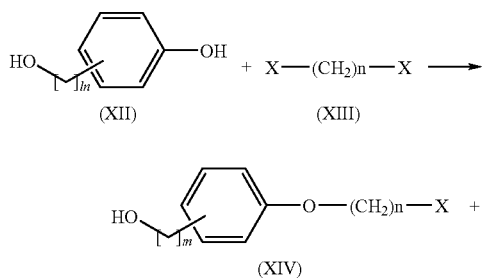

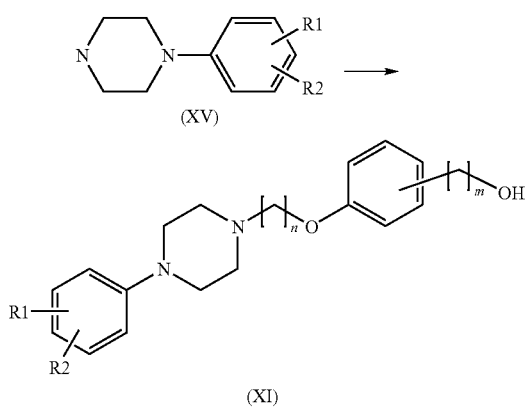

Details of the reaction conditions described in Reaction Scheme I are as follows. For the conversion of the compounds (XII) to the compound (XIV), the concentration of the starting material (XII) is about 0.005 to 0.1 moles with a dihalide alkane (XIII) ranging from about 2.0 to 3.0 equivalents and an organic or inorganic base from about 3.0 to 4.0 equivalents. This reaction is preferably refluxed. Then resulting product is purified by column chromatography. For the conversion of the compounds (XIV) to the compound (XI), a mixture of (XIV) and substituted phenylpiperazine (XV) was refluxed in 30 ml of acetonitrile for 6 h. For this coupling reaction, an ethereal solvent such as diethyl ether and tetrahydrofuran, a halogenated hydrocarbon solvent such as dichloromethane and chloroform, or a mixture thereof are used.

The method for preparing the O-carbamoyl phenyl piperazine compounds represented by the following General Structural Formula (VII) will be described below in detail.

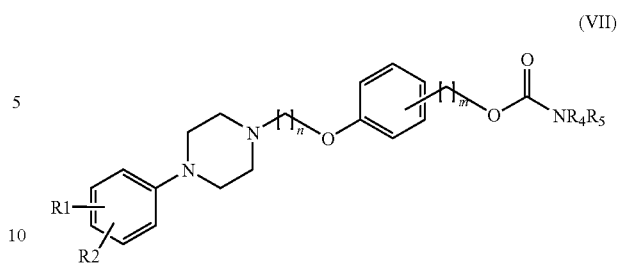

(VII)

Wherein, R1, R2, R4, R5, n, and m are as previously defined.

The O-carbamoyl phenyl piperazine compounds represented by the General Structural Formula (VII) are prepared by reacting hydroxy compounds represented by the General Structural Formula (XI) with 1,1'-carbonyldiimidazole and then with an amine base represented by the following General Structural Formula (XVI);

$R_4R_5NH$ (XVI)

The pharmaceutically acceptable salts thereof can be obtained by treating O-carbamoyl phenyl piperazine compounds VII with an anhydrous acid in a solution without further purification.

This procedure is summarized as set forth in Reaction Scheme II below.

Reaction Scheme II

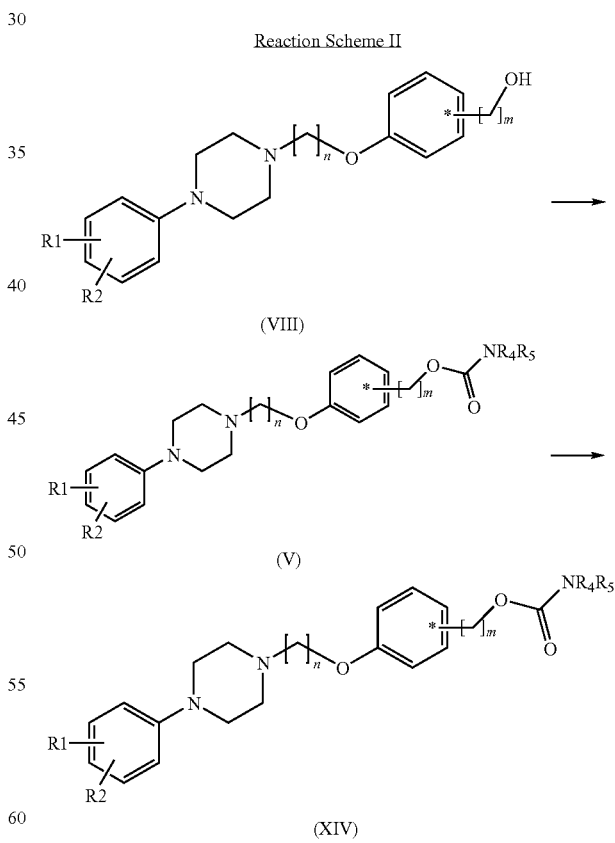

Details of the reaction conditions described in Reaction Scheme II are as follows. For the conversion of the compounds (XI) to the compound (VII), the concentration of the starting material (XI) is about 0.005 to 0.1 moles with 1,1'-carbonyldiimidazole ranging from about 2.0 to 3.0 equivalents. This reaction is preferably carried out at a temperature of 10 to 30° C. Without purification, the resulting intermediate is treated with 1 to 1000 equivalents of an amine base represented by the General Formula (XVI) at a temperature of 10 to 30° C. to give the compound of the General Formula (VII). For this carbamoylation, an ethereal solvent such as diethyl ether and tetrahydrofuran, a halogenated hydrocarbon solvent such as dichloromethane and chloroform, or a mixture thereof may be used.

In Reaction Scheme II, HA represents an acid that is capable of forming a pharmacologically useful salt with the basic nitrogen atom. Specific examples of the anhydrous acid used for the preparation of the compound (VII) from the compound (XVII) include hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzene sulfonic acid, methane sulfonic acid, ethane sulfonic acid, hydroxymethane sulfonic acid, hydroxyethane sulfonic acid, and the like. For additional acids, one can refer to "Pharmaceutical Salts", J. Pharm. Sci., 1977; 66(1): 1-19. This preparation is executed in a reaction media that can be exemplified by an ethereal solvent such as tetrahydrofuran, an alcoholic solvent such as methanol, an ester solvent such as ethyl acetate, a halogenated hydrocarbon solvent, and mixtures thereof. An ethereal solvent is recommended as an addition solution, including ethyl ether, propyl ether, isopropyl ether, butyl ether, and isobutyl ether. The concentration of the compound (VII) is in the order of about 0.01 to 5 moles.

In accordance with the present invention, the compound represented by the Structural Formula (I) and pharmaceutical acceptable salts thereof can be prepared by the following steps starting from amino phenyl piperazine compounds represented by the following General Structural Formula (XIX):

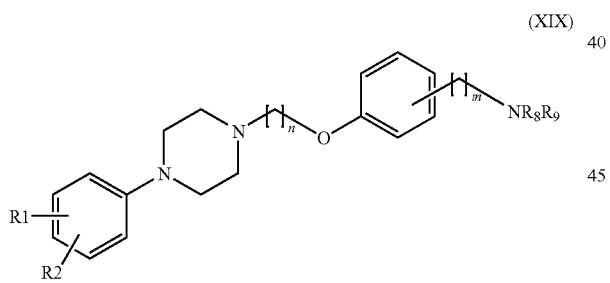
(XIX)

wherein, n is an integer from 2 to 6;

R1 is independently selected from the group consisting of hydrogen, a hydroxyl, a halogen, nitrogen dioxide, a straight or branched chain alkyl with 1 to 4 carbon atoms, and a straight or branched chain alkoxy of from 1 to 3 carbon atoms;

m is an integer from 1 to 3; and

R8 and R9 are the same or different and are independently selected from the group consisting of hydrogen, a straight or branched chain alkyl of from 1 to 4 carbon atoms and a phenyl.

The method for preparing the above amino phenyl piperazine compounds represented by the General Structural Formula (XIX) will be described below in detail.

The cyano phenol of Formula (XX) is reacted with dihalide alkane of Formula (XIII) to synthesize halogen compounds represented by the Structural Formula (XXI):

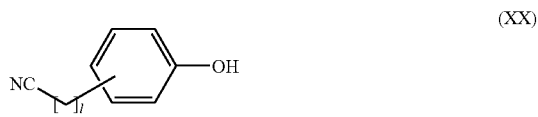
(XX)

wherein l is an integer from 0 to 2;

$$X-(CH_2)n-X \quad (XIII)$$

wherein n and X are the same as defined above; and

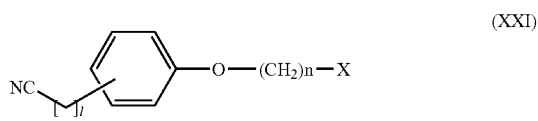
(XXI)

wherein n, l, and X are the same as defined above.

The halogen compound of Formula (XXI) is reacted with phenyl piperazine of Formula (XV) to synthesize cyano phenyl piperazine compounds of Formula (XXII):

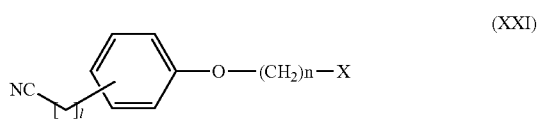
(XXI)

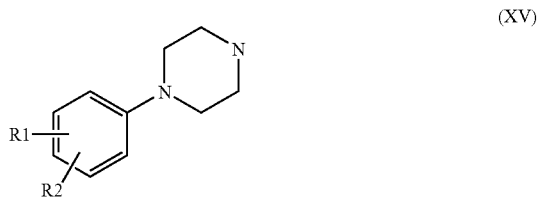
(XV)

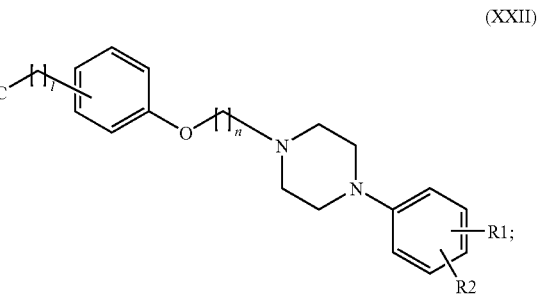
(XXII)

wherein R1, n, l, and X are the same as defined above.

The compounds of Formula (XXIII) are prepared by reacting cyano compounds of Formula (XXII) with a metal hydride.

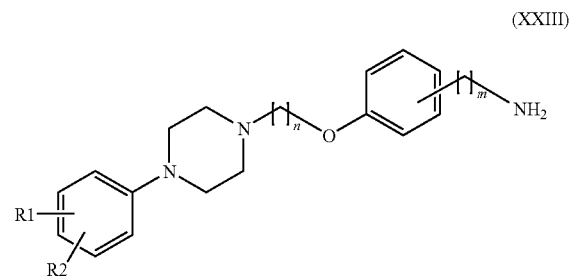
(XXIII)

The amino phenyl piperazine compounds represented by the General Structural Formula (XIX) are prepared by reacting compounds represented by the General Structural Formula (XXIII) for alkylation or arylation This procedure is summarized as set forth in Reaction Scheme IV below.

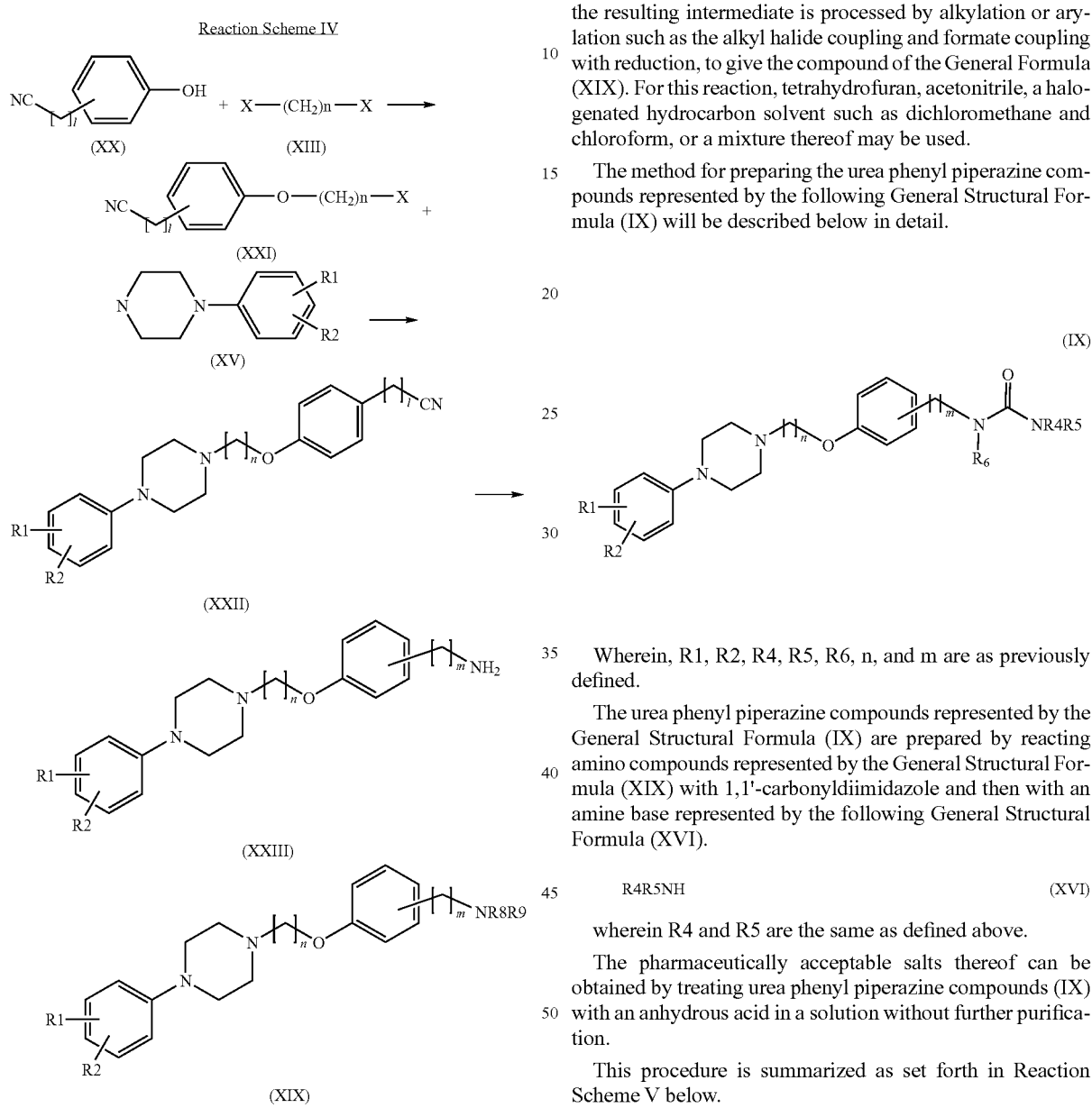

Details of the reaction conditions described in Reaction Scheme IV are as follows. For the conversion of the compounds (XX) to the compound (XXI), the concentration of the starting material (XX) is about 0.005 to 0.1 moles with dihalide alkane (XIII) ranging from about 2.0 to 3.0 equivalents and an organic or inorganic base from about 3.0 to 4.0 equivalents. This reaction is preferably refluxed. The resulting product is purified by column chromatography. For the conversion of the compounds (XXI) to the compound (XXII), a mixture of (XXI) and substituted phenylpiperazine (XV) was refluxed in 30 ml of acetonitrile for 6 h. For this coupling reaction, an ethereal solvent such as diethyl ether and tetrahydrofuran, a halogenated hydrocarbon solvent such as dichloromethane and chloroform, or the mixture thereof may be used. For the conversion of the compounds (XXII) to the compound (XXIII), the concentration of the starting material (XXII) is about 0.005 to 0.1 moles with a metal hydride ranging from about 2.0 to 3.0 equivalents. This reaction is preferably carried out at a temperature of 0° C. After the work-up process, the resulting intermediate is processed by alkylation or arylation such as the alkyl halide coupling and formate coupling with reduction, to give the compound of the General Formula (XIX). For this reaction, tetrahydrofuran, acetonitrile, a halogenated hydrocarbon solvent such as dichloromethane and chloroform, or a mixture thereof may be used.

The method for preparing the urea phenyl piperazine compounds represented by the following General Structural Formula (IX) will be described below in detail.

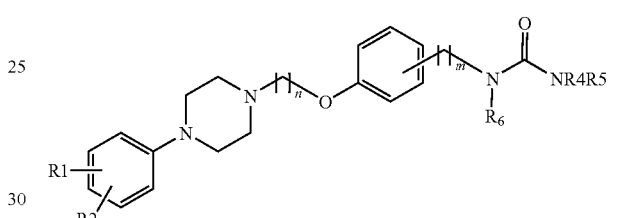

Wherein, R1, R2, R4, R5, R6, n, and m are as previously defined.

The urea phenyl piperazine compounds represented by the General Structural Formula (IX) are prepared by reacting amino compounds represented by the General Structural Formula (XIX) with 1,1'-carbonyldiimidazole and then with an amine base represented by the following General Structural Formula (XVI).

R4R5NH    (XVI)

wherein R4 and R5 are the same as defined above.

The pharmaceutically acceptable salts thereof can be obtained by treating urea phenyl piperazine compounds (IX) with an anhydrous acid in a solution without further purification.

This procedure is summarized as set forth in Reaction Scheme V below.

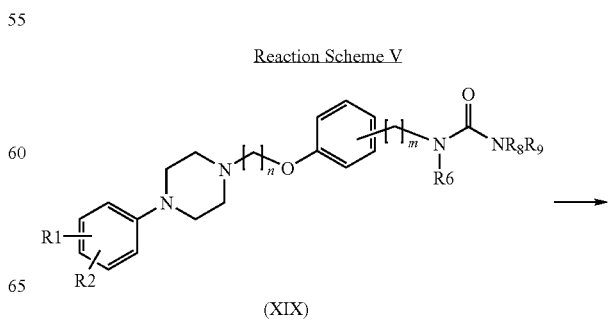

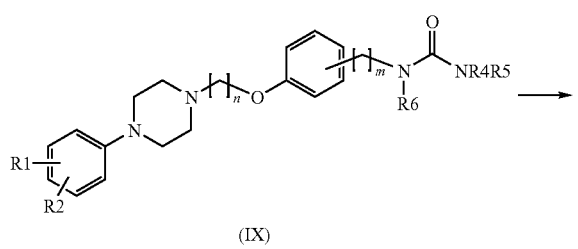

(IX)

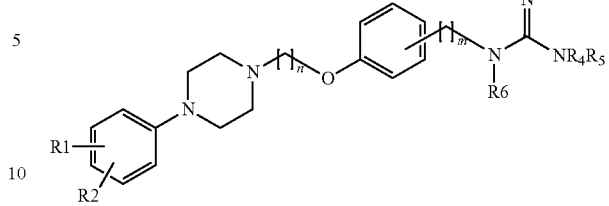

(X)

wherein

R1, R2, R4, R5, R6, n, and m are as previously defined.

The guanidyl phenyl piperazine compounds represented by the General Structural Formula (X) are prepared by reacting amino compounds represented by the General Structural Formula (XIX) with thiopseudoureas.

The pharmaceutically acceptable salts thereof can be obtained by treating urea phenyl piperazine compounds (X) with an anhydrous acid in a solution without further purification.

This procedure is summarized as set forth in Reaction Scheme VI below.

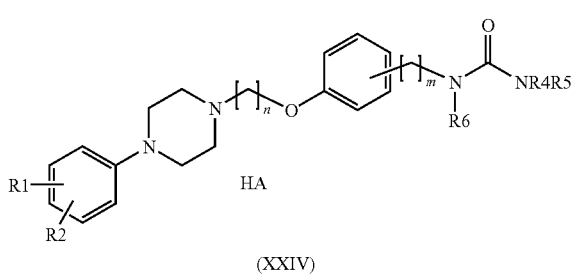

(XXIV)

Details of the reaction conditions described in Reaction Scheme V are as follows. For the conversion of the compounds (XIX) to the compound (IX), the concentration of the starting material (XIX) is about 0.005 to 0.1 moles with 1,1'-carbonyldiimidazole ranging from about 2.0 to 3.0 equivalents. This reaction is preferably carried out at a temperature of 10 to 30° C. Without purification, the resulting intermediate is treated with 1 to 1000 equivalents of an amine base represented by the General Formula (XVI) at a temperature of 10 to 30° C. to give the compound of the General Formula (IX). For this carbamoylation, an ethereal solvent such as diethyl ether and tetrahydrofuran, a halogenated hydrocarbon solvent such as dichloromethane and chloroform, or a mixture thereof may be used.

In Reaction Scheme V, HA represents an acid that is capable of forming a pharmacologically useful salt with the basic nitrogen atom. Specific examples of the anhydrous acid used for the preparation of the compound (IX) from the compound (XXIV) include hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzene sulfonic acid, methane sulfonic acid, ethane sulfonic acid, hydroxymethane sulfonic acid, hydroxyethane sulfonic acid, and the like. For additional acids, one can refer to "Pharmaceutical Salts", J. Pharm. Sci., 1977; 66(1): 1-19. This preparation is executed in a reaction media that can be exemplified by an ethereal solvent such as tetrahydrofuran, an alcoholic solvent such as methanol, an ester solvent such as ethyl acetate, a halogenated hydrocarbon solvent, and mixtures thereof. An ethereal solvent is recommended as an addition solution, including ethyl ether, propyl ether, isopropyl ether, butyl ether, and isobutyl ether. The concentration of the compound (IX) is in the order of about 0.01 to 5 moles.

The method for preparing the guanidyl phenyl piperazine compounds represented by the following General Structural Formula (X) will be described below in detail.

Reaction Scheme VI

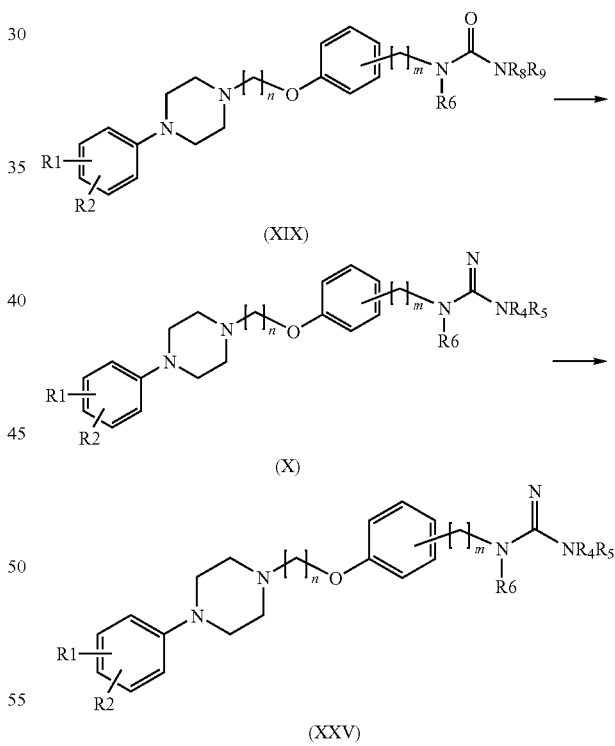

Details of the reaction conditions described in Reaction Scheme VI are as follows. For the conversion of the compounds (XIX) to the compound (X), the concentration of the starting material (XIX) is about 0.005 to 0.1 moles with thiopseudoureas ranging from about 2.0 to 3.0 equivalents. This reaction is preferably carried out at a temperature of 30 to 70° C. After reaction, the resulting product is worked up by acid and base. Then resulting product is purified by column chromatography. For this reaction, an ethereal solvent such as tetrahydrofuran, a halogenated hydrocarbon solvent such as dichloromethane and chloroform, or a mixture thereof may be used.

In Reaction Scheme VI, HA represents an acid that is capable of forming a pharmacologically useful salt with the basic nitrogen atom. Specific examples of the anhydrous acid used for the preparation of the compound (X) from the compound (XXV) include hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzene sulfonic acid, methane sulfonic acid, ethane sulfonic acid, hydroxymethane sulfonic acid, hydroxyethane sulfonic acid, and the like. For additional acids, one can refer to "Pharmaceutical Salts", J. Pharm. Sci., 1977; 66(1): 1-19. This preparation is executed in a reaction media that can be exemplified by an ethereal solvent such as tetrahydrofuran, an alcoholic solvent such as methanol, an ester solvent such as ethyl acetate, a halogenated hydrocarbon solvent, and mixtures thereof. An ethereal solvent is recommended as an addition solution, including ethyl ether, propyl ether, isopropyl ether, butyl ether, and isobutyl ether. The concentration of the compound (X) is in the order of about 0.01 to 5 moles. In another embodiment of the present invention, the present invention provides a pharmaceutical composition including an effective amount of phenyl piperazine compounds represented by Formula (I), and more preferably, the compounds represented by the above Structural Formulae VII, (IX), and (X), for treating CNS disorders such as psychosis and cognition disorders such as psychosis, schizophrenia, depression, and anxiety. In a further embodiment of the present invention, the present invention provides a method of treating CNS disorders such as psychosis, schizophrenia, depression, and anxiety in a mammal by administering an effective amount of the piperazine compounds represented by Structural Formula I, and more preferably, the compounds represented by Structural Formulae VII, (IX), and (X), alone or in combination with a pharmaceutical acceptable carrier or excipient to a mammal in need.

Compounds of the present invention may be used to treat a subject suffering from CNS disorders such as schizophrenia, (and other psychotic disorders such as paranoia), Parkinson's disease and other motor disorders, anxiety (e.g. generalized anxiety disorders, panic attacks, and obsessive compulsive disorders), depression (such as by the potentiation of serotonin reuptake inhibitors and serotonin norepinephrine reuptake inhibitors), Tourette's syndrome, migraines, autism, attention deficit disorders, and hyperactivity disorders. Compounds of the present invention may also be useful for the treatment of sleep disorders, social phobias, pain, thermoregulatory disorders, endocrine disorders, urinary incontinence, vasospasms, stroke, eating disorders such as obesity, anorexia, and bulimia, sexual dysfunction, and the treatment of alcohol, drug, and nicotine withdrawal.

This activity was examined through the anti-climbing behavior test and the anti-marble burying behavior test.

In therapeutic use as agents for various CNS disorders such as psychosis disorder, the compounds of the present invention are used, alone or in combination with pharmaceutically acceptable carrier or excipient.

The compounds of the present invention may be administered orally or parentally, neat or in combination with conventional pharmaceutical carriers. Applicable solid carriers can include one or more substances which may also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets may contain up to 99% of the active ingredient.

Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes, and ion exchange resins. Liquid carriers may be used in preparing solutions, suspensions, emulsions, syrups, and elixirs.

The active ingredient of this invention can be dissolved or suspended in a pharmaceutically acceptable liquid carrier such as water, an organic solvent, a mixture of both, or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g., cellulose derivatives, preferably a sodium carboxymethyl cellulose solution), alcohols (including monohydric alcohols and polyhydric alcohols, e.g., glycols) and their derivatives, and oils (e.g., fractionated coconut oil and arachis oil).

For parenteral administration the carrier can also be an oily ester such as ethyl oleate and isopropyl myristate. Sterile liquid carriers are used in sterile liquid form compositions for parenteral administration. Liquid pharmaceutical compositions that are sterile solutions or suspensions can be utilized by, for example, intramuscular, intraperitoneal, or subcutaneous injection. Sterile solutions can also be administered intravenously.

Oral administration may be either in liquid or solid composition form. Preferably, the pharmaceutical compositions containing the present compounds are in unit dosage form, e.g., as tablets or capsules. In such form, the composition is sub-divided in unit dosages containing appropriate quantities of the active ingredients. The unit dosage forms can be packaged compositions, for example, packaged powders, vials, ampoules, prefilled syringes or sachets containing liquids. Alternatively, the unit dosage form can be, for example, a capsule or tablet itself, or it can be the appropriate number of any such compositions in package form. The therapeutically effective dosage to be used may be varied or adjusted by the physician and generally ranges from 0.5 mg to 750 mg, according to the specific condition(s) being treated and the size, age, and response pattern of the patient.

The compounds of the present invention are administered to patients at a dosage of from 0.7 to 7000 mg per day. For a normal human adult with a body weight of approximately 70 kg, the administration amount is translated into a daily dose of 0.01 to 100 mg per kg of body weight. The specific dosage employed, however, may vary depending upon the requirements of the patient, the severity of the patient's condition, and the activity of the compound. The determination of optimum dosages for a particular situation must be clinically done and is within the skill of the art.

A better understanding of the present invention may be obtained in light of the following examples that are set forth to illustrate, but are not to be construed to limit, the present invention.

EXAMPLE 1

Carbamic acid 4-{4-[4-(2-methoxy-phenyl)-piperazine-1-yl]-butoxy}-benzyl ester

A mixture of 4-hydroxybenzaldehyde (5 mmol), 1-bromo-4-chlorobutane (5 mmol), and potassium carbonate (15 mmol) was refluxed in 100 ml of acetone for 6 h. This solution was then concentrated on a rotary evaporator and diluted with ethyl acetate. This mixture was then washed with brine, and the resulting organic layer was dried and purified by column chromatography. This was dissolved in methanol (50 ml) and was added with sodium borohydride (10 mmol) at 25° C., and stirred at 25° C. for 2 h. This solution was then concentrated in a rotary evaporator and diluted with methylene chloride, then washed with brine, and the resulting organic layer was dried and concentrated in vacuo. The crude product was dissolved in isopropanol (50 ml) and was added with 1-(2-methoxyphenyl)-piperazine (5 mmol), sodium carbonate (15 mmol), and potassium iodide (5 mmol) at 25° C., and the reaction mixture was refluxed for 12 h. This solution was then concentrated in a rotary evaporator and diluted with methylene chloride, then washed with brine, and the resulting organic layer was dried and purified by column chromatography. This product was dissolved in THF (50 ml) and was added with 1,1'-carbonyl diimidazole (12 mmol) at 0° C. The reaction mixture was stirred at room temperature for 4 h, followed by the addition of excess ammonium hydroxide (10 ml) at 0° C. After 5 h stirring at room temperature, water was added to terminate the reaction. The organic layer was extracted 3 times with dichloromethane, dried, and concentrated in vacuo. The residue was purified by column chromatography.

$^1$H-NMR (CDCl$_3$, 200 MHz) δ 7.3(m, 2H), 6.9(m, 6H), 5.0(s, 2H), 4.8(br, 2H), 4.0(t, 2H), 3.9(s, 3H), 3.1(m, 4H), 2.7(m, 4H), 2.5(t, 2H), 1.8(m, 4H)

EXAMPLE 2

Carbamic acid 4-{4-[4-(2-fluoro-phenyl)-piperazin-1-yl]-butoxy}-benzyl ester

The procedure given in Example 1 was followed using (2-fluorophenyl)-piperazine as a reactant, instead of (2-methoxyphenyl)-piperazine, to give carbamic acid 4-{4-[4-(2-fluoro-phenyl)-piperazin-1-yl]-butoxy}-benzyl ester.

$^1$H-NMR (CDCl$_3$, 200 MHz) δ 7.3(m, 2H), 6.9(m, 6H), 5.1(s, 2H), 4.8(br, 2H), 4.0(t, 2H), 3.2(m, 4H), 2.7(m, 4H), 2.5(t, 2H), 1.8(m, 4H)

EXAMPLE 3

Carbamic acid 4-[4-(4-phenyl-piperazin-1-yl)-butoxy]-benzyl ester

The procedure given in Example 1 was followed using 1-phenyl-piperazine as a reactant, instead of (2-methoxyphenyl)-piperazine, to give carbamic acid 4-[4-(4-phenyl-piperazin-1-yl)-butoxy]-benzyl ester.

$^1$H-NMR (CDCl$_3$, 200 MHz) δ 7.3(m, 4H), 6.9(m, 5H), 5.0(s, 2H), 4.8(br, 2H), 4.0(t, 2H), 3.1(m, 4H), 2.7(m, 4H), 2.5(t, 2H), 1.8(m, 4H)

EXAMPLE 4

Carbamic acid 4-{4-[4-(2-nitro-phenyl)-piperazin-1-yl]-butoxy}-benzyl ester

The procedure given in Example 1 was followed using (2-nitro-phenyl)-piperazine as a reactant, instead of (2-methoxyphenyl)-piperazine, to give carbamic acid 4-{4-[4-(2-nitro-phenyl)-piperazin-1-yl]-butoxy}-benzyl ester.

$^1$H-NMR (CDCl$_3$, 200 MHz) δ 7.3(m, 2H), 6.9(m, 6H), 5.1(s, 2H), 4.8(br, 2H), 4.0(t, 2H), 3.2(m, 4H), 2.7(m, 4H), 2.5(t, 2H), 1.8(m, 4H)

EXAMPLE 5

(4-{4-[4-(2-Methoxy-phenyl)-piperazin-1-yl]-butoxy}-benzyl)-urea

A mixture of 4-cyanophenol (5 mmol), 1-bromo-4-chlorobutane (5 mmol), and potassium carbonate (15 mmol) was refluxed in 100 ml of acetone for 6 h. This solution was then concentrated on a rotary evaporator and diluted with ethyl acetate. This mixture was then washed with brine, and the resulting organic layer was dried and purified by column chromatography. This product was dissolved in isopropanol (50 ml) and was added with 1-(2-methoxyphenyl)-piperazine (5 mmol), sodium carbonate (15 mmol), and potassium iodide (5 mmol) at 25° C., and the reaction mixture was refluxed for 12 h. This solution was then concentrated in a rotary evaporator and diluted with methylene chloride. This mixture was then washed with brine, and the resulting organic layer was dried and purified by column chromatography. This was dissolved in dried THF (50 ml) and was added with LAH (5 mmol) at 0° C., the reaction mixture was stirred at room temperature for 6 h, and H$_2$O:1N NaOH:H$_2$O (1:1:3) was added to terminate the reaction at 0° C. This crude product was dried with MgSO$_4$ and concentrated in vacuo, and the residue was purified by column chromatography. This product was dissolved in THF (50 ml) and was added with 1,1'-carbonyl diimidazole (12 mmol) at 0° C., the reaction mixture was stirred at room temperature for 4 h, followed by the addition of excess ammonium hydroxide (10 ml) at 0° C. After 5 h stirring at room temperature, water was added to terminate the reaction. The organic layer was extracted 3 times with dichloromethane, then dried and concentrated in vacuo, and the residue was purified by column chromatography.

$^1$H-NMR (CDCl$_3$, 200 MHz) δ 7.3(m, 2H), 6.9(m, 6H), 5.2(br,1H), 4.6 (br, 2H), 4.2 (d, 2H), 4.0(t, 2H), 3.9(s, 3H), 3.1(m, 4H), 2.7(m, 4H), 2.5(t, 2H), 1.8(m, 4H)

EXAMPLE 6

3-(4-{4-[4-(2-methoxy-phenyl)-piperazin-1-yl]-butoxy}-benzyl)-1,1-dimethyl-urea

The procedure given in Example 5 was followed using aq. dimethylamine as reactants, instead of ammonium hydroxide, to give 3-(4-{4-[4-(2-methoxy-phenyl)-piperazin-1-yl]-butoxy}-benzyl)-1,1-dimethyl-urea.

$^1$H-NMR (CDCl$_3$, 200 MHz) δ 7.3(m, 2H), 6.9(m, 6H), 4.6 (br, 1H), 4.4 (d, 2H), 4.0(t, 2H), 3.9(s, 3H), 3.1(m, 4H), 2.9(s, 6H), 2.7(m, 4H), 2.5(t, 2H), 1.8(m, 4H)

EXAMPLE 7

N-(4-{4-[4-(2-methoxy-phenyl)-piperazin-1-yl]-butoxy}-benzyl)-guanidine

A mixture of 4-cyanophenol (5 mmol), 1-bromo-4-chlorobutane (5 mmol), and potassium carbonate (15 mmol) was refluxed in 100 ml of acetone for 6 h. This solution was then concentrated in a rotary evaporator and diluted with ethyl acetate. This mixture was then washed with brine, and the resulting organic layer was dried and purified by column chromatography. This product was dissolved in isopropanol (50 ml) and was added with 1-(2-methoxyphenyl)-piperazine (5 mmol), sodium carbonate (15 mmol), and potassium iodide (5 mmol) at 25° C., and the reaction mixture was refluxed for 12 h. This solution was then concentrated in a rotary evaporator and diluted with methylene chloride. This mixture was then washed with brine, and the resulting organic layer was dried and purified by column chromatography. This was dissolved in dried THF (50 ml) and was added with LAH (5 mmol) at 0° C., the reaction mixture was stirred at room temperature for 6 h, and $H_2O:1N$ $NaOH:H_2O$ (1:1:3) was added to terminate the reaction at 0° C. This crude product was dried with MgSO4 and concentrated in vacuo, and the residue was purified by column chromatography. This product was dissolved in THF (50 ml) and trace water and was added with 1,3-bis(tert-butoxycarbonyl)-2-methyl-2-thiopseudourea (10 mmol). The reaction mixture was stirred at 52° C. After 3 h, the solvent was removed and the residue was treated with 5% $NaHCO_3$, then the organic layer was extracted 3 times with ethylacetate, then dried and concentrated in vacuo, and the residue was purified by column chromatography.

$^1$H-NMR (CDCl$_3$, 200 MHz) δ 8.0 (br, 1H), 7.3-6.9(m, 11H), 4.4 (br, 2H), 3.9(m, 5H), 3.2(m, 4H), 2.8(m, 4H), 2.5(t, 2H), 1.8(m, 4H)

EXAMPLE 8

(3-{4-[4-(2-methoxy-phenyl)-piperazin-1-yl]-butoxy}-benzyl)-urea

The procedure given in Example 5 was followed using 3-cyanophenol as reactants, instead of 4-cyanophenol, to give (3-{4-[4-(2-methoxy-phenyl)-piperazin-1-yl]-butoxy}-benzyl)-urea.

$^1$H-NMR (CDCl$_3$, 200 MHz) δ 7.3(m, 2H), 6.9(m, 6H), 5.0 (br, 1H), 4.4 (d, 2H), 4.0(t, 2H), 3.9(s, 3H), 3.7(s, 2H), 3.1(m, 4H), 2.7(m, 4H), 2.5(t, 2H), 1.8(m, 4H)

EXAMPLE 9

3-(3-{4-[4-(2-methoxy-phenyl)-piperazin-1-yl]-butoxy}-benzyl)-1,1-dimethyl-urea

The procedure given in Example 5 was followed using 3-cyanophenol and aq. dimethylamine as reactants, instead of 4-cyanophenol and ammonium hydroxide, to give 3-(3-{4-[4-(2-methoxy-phenyl)-piperazin-1-yl]-butoxy}-benzyl)-1,1-dimethyl-urea.

$^1$H-NMR (CDCl$_3$, 200 MHz) δ 7.3(m, 2H), 6.9(m, 6H), 4.6(br, 1H), 4.4(d, 2H), 4.0(t, 2H), 3.9(s, 3H), 3.1(m, 4H), 2.9(s, 6H), 2.7(m, 4H), 2.5(t, 2H), 1.8(m, 4H)

EXAMPLE 10

N-(3-{4-[4-(2-methoxy-phenyl)-piperazin-1-yl]-butoxy}-benzyl)-guanidine

The procedure given in Example 7 was followed using 3-cyanophenol as reactants, instead of 4-cyanophenol, to give N-(3-{4-[4-(2-methoxy-phenyl)-piperazin-1-yl]-butoxy}-benzyl)-guanidine.

$^1$H-NMR (CDCl$_3$, 200 MHz) δ 8.0(br, 1H), 7.3-6.9(m, 11H), 4.4(br, 2H), 4.0(m, 2H), 3.9(s, 3H), 3.2(m, 4H), 2.8(m, 4H), 2.5(t, 2H), 1.8(m, 4H)

EXAMPLE 11

Carbamic acid 4-{3-[4-(2-methoxy-phenyl)-piperazin-1-yl]-propoxy}-benzyl ester

The procedure given in Example 1 was followed using 1-bromo-3-chlorobutane as a reactant, instead of 1-bromo-4-chlorobutane, to give carbamic acid 4-{3-[4-(2-methoxy-phenyl)-piperazin-1-yl]-propoxy}-benzyl ester.

$^1$H-NMR (CDCl$_3$, 200 MHz) δ 7.3(m, 2H), 6.9(m, 6H), 5.0(s, 2H), 4.8(br, 2H), 4.1(t, 2H), 3.9(s, 3H), 3.1(m, 4H), 2.7(m, 4H), 2.6(t, 2H), 2.0(m, 2H)

EXAMPLE 12

Carbamic acid 4-{2-[4-(2-methoxy-phenyl)-piperazin-1-yl]-ethoxy}-benzyl ester

The procedure given in Example 1 was followed using 1-bromo-2-chlorobutane as a reactant, instead of 1-bromo-4-chlorobutane, to give carbamic acid 4-{2-[4-(2-methoxy-phenyl)-piperazin-1-yl]-ethoxy}-benzyl ester.

$^1$H-NMR (CDCl$_3$, 200 MHz) δ 7.3(m, 2H), 6.9(m, 6H), 5.0(s, 2H), 4.8(br, 2H), 4.2(t, 2H), 3.9(s, 3H), 3.1(m, 4H), 2.9(t, 2H), 2.8(m, 4H)

EXAMPLE 13

Carbamic acid 4-{5-[4-(2-methoxy-phenyl)-piperazin-1-yl]-pentyloxy}-benzyl ester The procedure given in Example 1 was followed using 1-bromo-5-chlorobutane as a reactant, instead of 1-bromo-4-chlorobutane, to give carbamic acid 4-{5-[4-(2-methoxy-phenyl)-piperazin-1-yl]-pentyloxy}-benzyl ester.

$^1$H-NMR (CDCl$_3$, 200 MHz) δ 7.3(m, 2H), 6.9(m, 6H), 5.0(s, 2H), 4.8(br, 2H), 4.1(t, 2H), 3.9(s, 3H), 3.1(m, 4H), 2.7(m, 4H), 2.5(t, 2H), 1.8(m, 2H), 1.6(m, 4H)

EXAMPLE 14

1-(4-{4-[4-(2-chloro-phenyl)-piperazin-1-yl]-butoxy}-benzyl)-1-methyl-urea

A mixture of 4-cyanophenol (5 mmol), 1-bromo-4-chlorobutane (5 mmol), and potassium carbonate (15 mmol) was refluxed in 100 ml of acetone for 6 h. This solution was then concentrated in a rotary evaporator and diluted with ethyl acetate. This mixture was then washed with brine, and the resulting organic layer was dried and purified by column chromatography. This product was dissolved in isopropanol (50 ml) and was added with 1-(2-chloro-phenyl)-piperazine (5 mmol), sodium carbonate (15 mmol), and potassium iodide (5 mmol) at 25° C., and the reaction mixture was refluxed for 12 h. This solution was then concentrated in a rotary evaporator and diluted with methylene chloride, this mixture was then washed with brine, and the resulting organic layer was dried and purified by column chromatography. This was dissolved in dried THF (50 ml) and was added with LAH (5 mmol) at 0° C., the reaction mixture was stirred at room temperature for 6 h, and $H_2O:1N$ $NaOH:H_2O$ (1:1:3) was added to terminate the reaction at 0° C. This crude product was dried with MgSO$_4$ and concentrated in vacuo, and the residue was purified by column chromatography. The product was added to ethylchloroformate (5 mmol) and triethylamine (6 mmol), at 0° C. and was stirred for 2 hr in 20 ml of dichloromethane. This solution was diluted with dichloromethane and washed with water, and the resulting organic layer was dried and concentrated in vacuo. This was dissolved in dried THF and was added with LAH (5 mmol) at 0° C. The reaction mixture was stirred at room temperature for 6 h, and H2O:1N NaOH:H$_2$O (1:1:3) was added to terminate the reaction at 0° C. This crude product was dried with MgSO$_4$ and concentrated in vacuo. This product was dissolved in THF (20 ml) and was added with 1,1'-carbonyl diimidazole (12 mmol) at 0° C. The reaction mixture was stirred at room temperature for 4 h, followed by the addition of excess ammonium hydroxide (10 ml) at 0° C. After 5 h stirring at room temperature, water was added to terminate the reaction. The organic layer was extracted 3 times with dichloromethane, then dried and concentrated in vacuo. The residue was purified by column chromatography.

$^1$H-NMR (CDCl$_3$, 200 MHz) δ 7.3(m, 2H), 6.9(m, 6H), 4.6 (br, 2H), 4.2 (d, 2H), 4.0(t, 2H), 3.1(m, 4H), 2.9(s, 3H), 2.7(m, 4H), 2.5(t, 2H), 1.8(m, 4H)

EXAMPLE 15

1-(4-{4-[4-(2-methoxy-phenyl)-piperazin-1-yl]-butoxy}-benzyl)-3-methyl-urea

The procedure given in Example 5 was followed using aqueous dimethylamine as reactants, instead of ammonium hydroxide, to give (1-(4-{4-[4-(2-methoxy-phenyl)-piperazin-1-yl]-butoxy}-benzyl)-3-methyl-urea.

$^1$H-NMR (CDCl$_3$, 200 MHz) δ 7.3(m, 2H), 6.9(m, 6H), 5.2(br, 1H), 4.6 (br, 1H), 4.2 (d, 2H), 4.0(t, 2H), 3.9(s, 3H), 3.1(m, 4H), 2.9(s, 3H), 2.7(m, 4H), 2.5(t, 2H), 1.8(m, 4H)

EXAMPLE 16

1-(4-{4-[4-(2,3-dichloro-phenyl)-piperazin-1-yl]-butoxy}-benzyl)-1,3,3-trimethyl-urea The procedure given in Example 14 was followed using 1-(2,3-dichloro-phenyl)-piperazine and aqueous dimethylamine as reactants, instead of 1-(2-methoxyphenyl)-piperazine and ammonium hydroxide, to give 1-(4-{4-[4-(2,3-dichloro-phenyl)-piperazin-1-yl]-butoxy}-benzyl)-1,3,3-trimethyl-urea.

$^1$H-NMR (CDCl$_3$, 200 MHz) δ 7.3(m, 2H), 6.9(m, 7H), 4.2 (d, 2H), 4.0(t, 2H), 3.1(m, 4H), 2.9(s, 6H), 2.8(s, 3H), 2.7(m, 4H), 2.5(t, 2H), 1.8(m, 4H)

EXAMPLE 17

1-(4-{4-[4-(2-chloro-phenyl)-piperazin-1-yl]-butoxy}-benzyl)-1-methyl-3-phenyl-urea A mixture of 4-cyanophenol (5 mmol), 1-bromo-4-chlorobutane (5 mmol), and potassium carbonate (15 mmol) was refluxed in 100 ml of acetone for 6 h. This solution was then concentrated in a rotary evaporator and diluted with ethyl acetate. This mixture was then washed with brine, and the resulting organic layer was dried and purified by column chromatography. This product was dissolved in isopropanol (50 ml) and was added with 1-(2-chloro-phenyl)-piperazine (5 mmol), sodium carbonate (15 mmol), and potassium iodide (5 mmol) at 25° C., and the reaction mixture was refluxed for 12 h. This solution was then concentrated in a rotary evaporator and diluted with methylene chloride. This mixture was then washed with brine, and the resulting organic layer was dried and purified by column chromatography. This was dissolved in dried THF (50 ml) and was added with LAH (5 mmol) at 0° C. The reaction mixture was stirred at room temperature for 6 h, and H2O:1N NaOH:H$_2$O (1:1:3) was added to terminate the reaction at 0° C. This crude product was dried with MgSO$_4$ and concentrated in vacuo. The residue was purified by column chromatography. The product was added to ethylchloroformate (5 mmol) and triethylamine (6 mmol) at 0° C. and was stirred for 2 hr in 20 ml of dichloromethane. This solution was diluted with dichloromethane and washed with water, and the resulting organic layer was dried and concentrated in vacuo. This was dissolved in dried THF and was added with LAH (5 mmol) at 0° C. The reaction mixture was stirred at room temperature for 6 h, and H2O:1N NaOH:H$_2$O (1:1:3) was added to terminate the reaction at 0° C. This crude product was dried with MgSO$_4$ and concentrated in vacuo. This product was dissolved in dichloromethane (20 ml) and was added with phenylisocyante (6 mmol). The reaction mixture was stirred at room temperature for 4 h, and water was added to terminate the reaction. The organic layer was extracted 3 times with dichloromethane, then dried and concentrated in vacuo, and the residue was purified by column chromatography.

$^1$H-NMR (CDCl$_3$, 200 MHz) δ 7.2 (m, 2H), 7.0-6.7 (m, 6H), 5.5 (s, 2H), 4.0(t, 2H), 3.8(s, 3H), 3.1(m, 4H), 2.7(m, 4H), 2.5(t, 2H), 2.5(s, 3H),1.8(m, 4H)

EXAMPLE 18

Anti-Climbing Behavior Test

The anti-climbing test evaluates suppression of the climbing behavior induced by apomorphine in mice. A designated amount of the test compound was intraperitoneally administered to several groups of ICR CD strain male mice (body weight, 20 to 25 g; one group, 6 mice), and each of the animals was charged in an individual column cage of 12 cm in diameter and 14 cm in height having metal poles (each pole, 2 mm in diameter) vertically installed and arranged along the periphery at an interval of 1 cm.

Compounds to be tested for antipsychotic activity were injected intraperitoneally at various time intervals, e.g. 30 minutes, 60 minutes, etc., prior to the apomorphine challenge at a screening dose of 2 mg/kg.

For evaluation of climbing, 3 readings were taken at 10, 20, and 30 minutes after apomorphine administration according to the following scale as indicated in Table 1

TABLE 1

| Score | Evaluation |
|---|---|
| 0 | All the paws were on the floor |
| 1 | One paw seized the pole of the cage |
| 2 | Two paws seized the pole of the cage |
| 3 | Three paws seized the pole of the cage |
| 4 | All four paws seized the pole of the cage |

Mice that were consistently climbing before the injection of apomorphine were discarded.

With full-developed apomorphine climbing, the animals were hanging on to the cage walls, rather motionless, over longer periods of time. By contrast, climbs due to mere motor stimulation usually only last a few seconds.

The climbing scores were individually totaled (maximal score: 12 per mouse over readings) and the total score of the control group (vehicle intraperitoneally-apomorphine subcutaneously) was set to 100%. Anti-climbing data are presented in Table 2.

TABLE 2

| COMPOUND | % reduction at 5 mg/kg, ip |
| --- | --- |
| Carbamic acid 4-{4-[4-(2-methoxy-phenyl)-piperazin-1-yl]-butoxy}-benzyl ester | 97 |
| Carbamic acid 4-{4-[4-(2-fluoro-phenyl)-piperazin-1-yl]-butoxy}-benzyl ester | 100 |
| Carbamic acid 4-[4-(4-phenyl-piperazin-1-yl)-butoxy]-benzyl ester | 4.2 |
| Carbamic acid 4-{4-[4-(2-nitro-phenyl)-piperazin-1-yl]-butoxy}-benzyl ester | 15.5 |
| (4-{4-[4-(2-methoxy-phenyl)-piperazin-1-yl]-butoxy}-benzyl)-urea | 81 |
| 3-(4-{4-[4-(2-methoxy-phenyl)-piperazin-1-yl]-butoxy}-benzyl)-1,1-dimethyl-urea | 37 |
| N-(4-{4-[4-(2-methoxy-phenyl)-piperazin-1-yl]-butoxy}-benzyl)-guanidine | 30 |
| (3-{4-[4-(2-methoxy-phenyl)-piperazin-1-yl]-butoxy}-benzyl)-urea | 18.3 |
| N-(3-{4-[4-(2-methoxy-phenyl)-piperazin-1-yl]-butoxy}-benzyl)-guanidine | 22.2 |
| Carbamic acid 4-{3-[4-(2-methoxy-phenyl)-piperazin-1-yl]-propoxy}-benzyl ester | 83.3 |
| Carbamic acid 4-{2-[4-(2-methoxy-phenyl)-piperazin-1-yl]-ethoxy}-benzyl ester | 36.1 |
| Carbamic acid 4-{5-[4-(2-methoxy-phenyl)-piperazin-1-yl]-pentyloxy}-benzyl ester | 73.6 |
| Quetiapine | 53.5 |
| Aripiprazole | 83.6 |
| Olanzapine | 88.5 |

An anti-dopaminergic effect through the D2 receptor as with other antipsychotic drugs suggested effectiveness of these compounds in treating psychosis such as schizophrenia.

EXAMPLE 19

Anti-Marble Burying Behavior Test

Marble burying was developed and validated as a preclinical assay of potential anxiolytic activity (Andrews and Broekkamp (1993). Procedures to Identify Anxiolytic or Anxiogenic agents. In Behavioural Neuroscience, ed. A Sahgal, pp. 37-54. IRL Press, Oxford). The marble burying test places a naive mouse into a novel environment containing 25 marbles (arranged on top of a sawdust surface). A reduction in the number of marbles buried by the mouse was hypothesized to be an anxiolytic-like effect. Anti-marble burying data are presented in Table 3.

TABLE 3

| COMPOUND | % reduction at 3 mg/kg, ip |
| --- | --- |
| Carbamic acid 4-{4-[4-(2-methoxy-phenyl)-piperazin-1-yl]-butoxy}-benzyl ester | 81.0 |
| Carbamic acid 4-{4-[4-(2-nitro-phenyl)-piperazin-1-yl]-butoxy}-benzyl ester | 12.4 |
| (4-{4-[4-(2-methoxy-phenyl)-piperazin-1-yl]-butoxy}-benzyl)-urea | 90.1 |
| N-(4-{4-[4-(2-methoxy-phenyl)-piperazin-1-yl]-butoxy}-benzyl)-guanidine | 11 |
| (3-{4-[4-(2-methoxy-phenyl)-piperazin-1-yl]-butoxy}-benzyl)-urea | 18.3 |
| N-(3-{4-[4-(2-methoxy-phenyl)-piperazin-1-yl]-butoxy}-benzyl)-guanidine | 72.4 |
| Carbamic acid 4-{3-[4-(2-methoxy-phenyl)-piperazin-1-yl]-propoxy}-benzyl ester | 6.1 |
| Carbamic acid 4-{2-[4-(2-methoxy-phenyl)-piperazin-1-yl]-ethoxy}-benzyl ester | 10.1 |
| Carbamic acid 4-{5-[4-(2-methoxy-phenyl)-piperazin-1-yl]-pentyloxy}-benzyl ester | 4.1 |
| Buspirone | 56.0 (20 mg/kg, ip) |

An anti-marble burying effect, as with other anti-anxiety drugs, suggested potentials for treating psychosis such as anxiety.

We claim:

1. A piperazine compound represented by Formula (I) or pharmaceutically acceptable salts thereof,

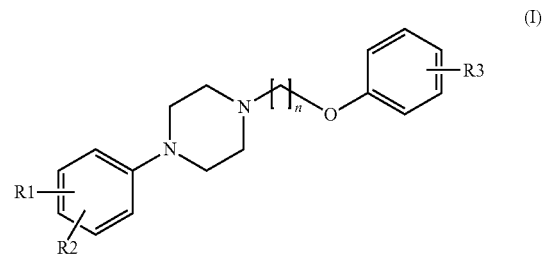

wherein n is an integer from 2 to 6, $R_1$ and $R_2$ are the same or different and are independently selected from the group consisting of hydrogen, a hydroxyl, a halogen, nitrogen dioxide, a straight or branched chain alkyl group with 1 to 4 carbon atoms, and a straight or branched chain alkoxy group with 1 to 4 carbon atoms, and $R_3$ is selected from the following groups:

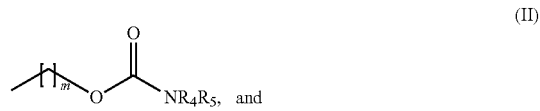

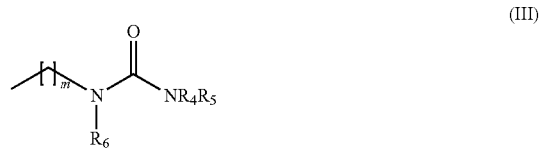

wherein m is an integer from 1 to 3, $R_4$ and $R_5$ are the same or different and are independently selected from the group consisting of hydrogen, a straight or branched chain alkyl group with 1 to 4 carbon atoms, and a benzyl, and optionally $R_4$ and $R_5$ form a 5 to 7-membered heterocyclic ring together with nitrogen atoms to which they are attached, and $R_6$ is selected from the group consisting of hydrogen, a straight or branched chain alkyl group with 1 to 4 carbon atoms, and a phenyl.

2. The piperazine compound of claim 1, wherein the compound is an O-carbamoyl phenyl piperazine compound represented by Formula (VII) or pharmaceutically acceptable salts thereof,

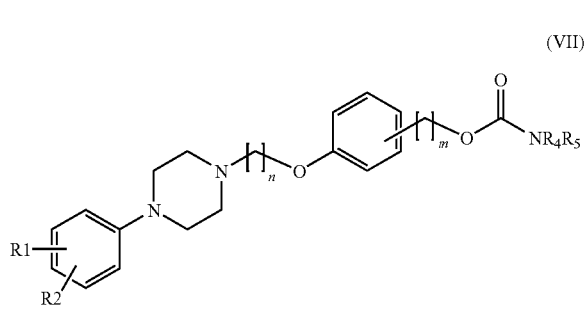

(VII)

wherein:

n is an integer of 2 to 6;

$R_1$ and $R_2$ are the same or different and are independently selected from the group consisting of hydrogen, a hydroxyl, a halogen, nitrogen dioxide, a straight or branched chain alkyl group with 1 to 4 carbon atoms, and a straight or branched chain alkoxy group with 1 to 4 carbon atoms;

m is an integer from 1 to 3; and $R_4$ and $R_5$ are the same or different and are independently selected from the group consisting of hydrogen, a straight or branched chain alkyl group with 1 to 4 carbon atoms, and a benzyl, and optionally $R_4$ and $R_5$ form a 5 to 7-membered heterocyclic ring together with nitrogen atoms to which they are attached.

3. The piperazine compound of claim 1, wherein the compound is a urea phenyl piperazine compound represented by the following Structural Formula (IX) or pharmaceutically acceptable salts thereof,

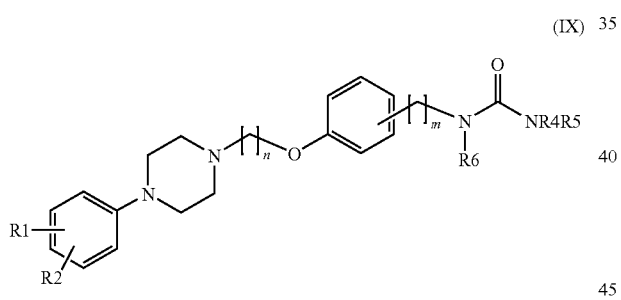

(IX)

wherein:

n is an integer of 2 to 6;

$R_1$ and $R_2$ are the same or different and are independently selected from the group consisting of hydrogen, a hydroxyl, a halogen, nitrogen dioxide, a straight or branched chain alkyl group with 1 to 4 carbon atoms, and a straight or branched chain alkoxy group with 1 to 3 carbon atoms;

m is an integer of 1 to 3;

$R_4$ and $R_5$ are the same or different and are independently selected from the group consisting of hydrogen, a straight or branched chain alkyl group with 1 to 4 carbon atoms and a benzyl, and optionally $R_4$ and $R_5$ form a 5 to 7-membered heterocyclic ring together with nitrogen atoms to which they are attached; and $R_6$ is selected from the group consisting of hydrogen, a straight or branched chain alkyl with 1 to 4 carbon atoms, and a phenyl.

4. The compound in accordance with claim 2, wherein said compound is carbamic acid 4-{4-[4-(2-methoxy-phenyl)-piperazin-1-yl]-butoxy}-benzyl ester, carbamic acid 4-{3-[4-(2-methoxy-phenyl)-piperazin-1-yl]-propoxy}-benzyl ester, carbamic acid 4-{5-[4-(2-methoxy-phenyl)-piperazin-1-yl]-ethoxy}-benzyl ester, carbamic acid 4-{5-[4-(2-methoxy-phenyl)-piperazin-1-yl]-pentyloxy}-benzyl ester, or carbamic acid 4-{4-[4-(2-fluoro-phenyl)-piperazin-1-yl]-butoxy}-benzyl ester.

5. The compound in accordance with claim 3, wherein said compound is (4-{4-[4-(2-methoxy-phenyl)-piperazin-1-yl]-butoxy}-benzyl)-urea, (3-{4-[4-(2-methoxy-phenyl)-piperazin-1-yl]-butoxy}-benzyl)-urea, 1-(4-(4-{4-[4-(2-chloro-phenyl)-piperazin-1-yl]-butoxy}-benzyl)-1-methyl-urea, 3-(4-{4-[4-(2-methoxy-phenyl)-piperazin-1-yl]-butoxy}-benzyl)-1,1-dimethyl-urea, 3-(3-{4-[4-(2-methoxy-phenyl)-piperazin-1-yl]-butoxy}-benzyl)-1,1-dimethyl-urea, 1-(4-{4-[4-(2-methoxy-phenyl)-piperazin-1-yl]-butoxy}-benzyl)-3-methyl-urea, 1-(4-{4-[4-(2,3-dichloro-phenyl)-piperazin-1-yl]-butoxy}-benzyl)-1,3,3-trimethyl-urea, or 1-(4-{4-[4(2-chloro-phenyl)-piperazin-1-yl]-butoxy}-benzyl)-1-methyl-3-phenyl-urea.

6. A pharmaceutical composition comprising an effective amount of the piperazine compound of claim 1 and a pharmaceutically acceptable carrier or excipient.

7. The pharmaceutical composition of claim 6, wherein the composition comprises an effective amount of an O-carbamoyl phenyl piperazine compound represented by Formula (VII) or pharmaceutically acceptable salts thereof,

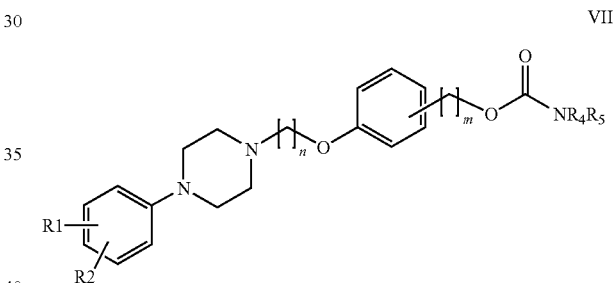

VII wherein:

n is an integer of 2 to 6;

$R_1$ and $R_2$ are the same or different and are independently selected from the group consisting of hydrogen, a hydroxyl, a halogen, nitrogen dioxide, a straight or branched chain alkyl group of from 1 to 4 carbon atoms, and a straight or branched chain alkoxy group with 1 to 4 carbon atoms;

m is an integer of 1 to 3; and $R_4$ and $R_5$ are the same or different and are independently selected from the group consisting of hydrogen, a straight or branched chain alkyl group with 1 to 4 carbon atoms, and a benzyl, and optionally $R_4$ and $R_5$ form a 5 to 7-membered heterocyclic ring together with nitrogen atoms to which they are attached.

8. The pharmaceutical composition of claim 7, wherein the compound is carbamic acid 4-{4-[4-(2-methoxy-phenyl)-piperazin-1-yl]-butoxy}-benzyl ester, carbamic acid 4-{3-[4-(2-methoxy-phenyl)-piperazin-1-yl]-propoxy}-benzyl ester, carbamic acid 4-{2-[4-(2-methoxy-phenyl)-piperazin-1-yl]-ethoxy}-benzyl ester, carbamic acid 4-{5-[4-(2-methoxy-phenyl)-piperazin-1-yl]-pentyloxy}-benzyl ester, or carbamic acid 4-{4-[4-(2-fluoro-phenyl)-piperazin-1-yl]-butoxy}-benzyl ester.

9. The pharmaceutical composition of claim 6, wherein the composition comprises an effective amount of a urea phenyl piperazine compound represented by Formula (IX) or pharmaceutically acceptable salts thereof,

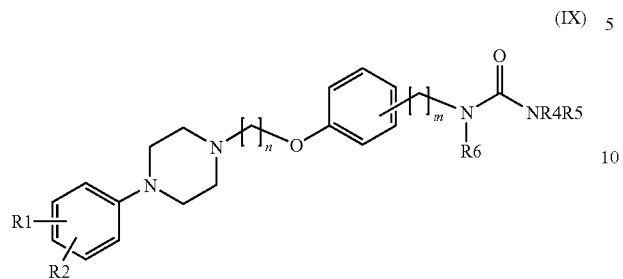

wherein:
n is an integer of 2 to 6;
$R_1$ and $R_2$ are the same or different and are independently selected from the group consisting of hydrogen, a hydroxyl, a halogen, nitrogen dioxide, a straight or branched chain alkyl group with 1 to 4 carbon atoms, and a straight or branched chain alkoxy group with 1 to 4 carbon atoms;
m is an integer of 1 to 3;

$R_4$ and $R_5$ are the same or different and are independently selected from the group consisting of hydrogen, a straight or branched chain alkyl group with 1 to 4 carbon atoms, and benzyl, and optionally $R_4$ and $R_5$ form a 5 to 7-membered heterocyclic ring together with nitrogen atoms to which they are attached; and $R_6$ is selected from the group consisting of hydrogen, a straight or branched chain alkyl with 1 to 4 carbon atoms, and a phenyl.

10. The pharmaceutical composition of claim 9, wherein said compound is 4-{4-[4-(2-methoxy-phenyl)-piperazin-1-yl]butoxy}-benzyl)-urea, (3-{4-[4(2-methoxy-phenyl)-piperazin -1-yl]-butoxy}-benzyly)urea, 1-(4-{4-[4-(2-chloro-phenyl)-piperazin-1-yl]-butoxy}-benzyl)-1-methyl-urea, 3-(4-{4-[4-(2-methoxy-phenyl)-piperazin-1-yl]-butoxy}-benzyl)-1,1-dimethyl-urea, 3-(3-{4-[4-(2-methoxy-phenyl)-piperazin-1-yl]-butoxy}-benzyl)-1,1-dimethyl-urea, 1-(4-{4-[4(2-methoxy -phenyl)-piperazin-1-yl]-butoxy}-benzyl)-3-methyl-urea, 1-(4-{4-[4-(2,3-dichloro-phenyl)-piperazin -1-yl]-butoxy}-benzyl)-1,3,3-trimethyl-urea, or 1-(4-{4-[4-(2-chloro-phenyl)-piperazin-1-yl ]-butoxy}-benzyl)-1-methyl-3-phenyl-urea.

* * * * *